United States Patent
Van Slyke et al.

(10) Patent No.: US 9,560,978 B2
(45) Date of Patent: Feb. 7, 2017

(54) SYSTEMS AND METHODS FOR DETERMINING RESPIRATION INFORMATION FROM A PHYSIOLOGICAL SIGNAL USING AMPLITUDE DEMODULATION

(71) Applicant: Covidien LP, Mansfield, MA (US)

(72) Inventors: Braddon M. Van Slyke, Arvada, CO (US); Ronald Kadlec, Arvada, CO (US); Scott McGonigle, Edinburgh (GB)

(73) Assignee: Covidien LP, Mansfield, MA (US)

( * ) Notice: Subject to any disclaimer, the term of this patent is extended or adjusted under 35 U.S.C. 154(b) by 694 days.

(21) Appl. No.: 13/759,943

(22) Filed: Feb. 5, 2013

(65) Prior Publication Data

US 2014/0221851 A1    Aug. 7, 2014

(51) Int. Cl.
| | |
|---|---|
| A61B 5/02 | (2006.01) |
| A61B 5/024 | (2006.01) |
| A61B 5/0205 | (2006.01) |
| A61B 5/00 | (2006.01) |
| A61B 5/08 | (2006.01) |
| A61B 5/1455 | (2006.01) |

(52) U.S. Cl.
CPC ......... *A61B 5/02416* (2013.01); *A61B 5/0205* (2013.01); *A61B 5/02433* (2013.01); *A61B 5/0803* (2013.01); *A61B 5/7203* (2013.01); *A61B 5/7278* (2013.01); *A61B 5/14551* (2013.01)

(58) Field of Classification Search
CPC ..................................................... A61B 7/003
See application file for complete search history.

(56) References Cited

U.S. PATENT DOCUMENTS

| | | | |
|---|---|---|---|
| 3,846,704 | A | 11/1974 | Bessette |
| 4,063,551 | A | 12/1977 | Sweeney |
| 4,458,518 | A | 7/1984 | Ingle |
| 4,958,638 | A | 9/1990 | Sharpe et al. |
| 5,188,108 | A | 2/1993 | Secker |
| 5,285,783 | A | 2/1994 | Secker |
| 5,285,784 | A | 2/1994 | Seeker |

(Continued)

FOREIGN PATENT DOCUMENTS

| | | |
|---|---|---|
| EP | 0072601 A1 | 2/1983 |
| EP | 1344488 A2 | 9/2004 |

(Continued)

OTHER PUBLICATIONS

Long, S. "Phase Locked Loop Circuits." Apr. 27, 2005. https://web.archive.org/web/20081201083334/http://www.ece.ucsb.edu/~long/ece594a/PLL_intro594a_s05.pdf.

(Continued)

*Primary Examiner* — Patricia Mallari
*Assistant Examiner* — Vasuda Ramachandran
(74) *Attorney, Agent, or Firm* — Shvarts & Leiz LLP

(57) ABSTRACT

A patient monitoring system may receive a physiological signal such as a photoplethysmograph (PPG) signal. The PPG signal may include a pulsatile component that functions as a carrier signal and an amplitude modulation component that represents respiration information. The patient monitoring system may move the amplitude modulation component to a baseline component of the PPG signal. Respiration information may be calculated based on the amplitude modulation component.

9 Claims, 8 Drawing Sheets

(56) References Cited

U.S. PATENT DOCUMENTS

| | | |
|---|---|---|
| 5,368,026 A | 11/1994 | Swedlow et al. |
| 5,398,682 A | 3/1995 | Lynn |
| 5,558,096 A | 9/1996 | Palatnik |
| 5,584,295 A | 12/1996 | Muller et al. |
| 5,588,425 A | 12/1996 | Sackner et al. |
| 5,595,176 A | 1/1997 | Yamaura |
| 5,605,151 A | 2/1997 | Lynn |
| 5,862,805 A | 1/1999 | Nitzan |
| 5,865,736 A | 2/1999 | Baker et al. |
| 5,891,023 A | 4/1999 | Lynn |
| 6,002,952 A | 12/1999 | Diab et al. |
| 6,035,223 A | 3/2000 | Baker |
| 6,081,742 A | 6/2000 | Amano et al. |
| 6,095,984 A | 8/2000 | Amano et al. |
| 6,129,675 A | 10/2000 | Jay |
| 6,135,966 A | 10/2000 | Ko |
| 6,178,261 B1 | 1/2001 | Williams et al. |
| 6,223,064 B1 | 4/2001 | Lynn et al. |
| 6,229,856 B1 | 5/2001 | Diab et al. |
| 6,238,351 B1 | 5/2001 | Orr et al. |
| 6,325,761 B1 | 12/2001 | Jay |
| 6,334,065 B1 | 12/2001 | Al-Ali et al. |
| 6,342,039 B1 | 1/2002 | Lynn et al. |
| 6,350,242 B1 | 2/2002 | Doten et al. |
| 6,405,076 B1 | 6/2002 | Taylor et al. |
| 6,449,501 B1 | 9/2002 | Reuss |
| 6,463,311 B1 | 10/2002 | Diab |
| 6,506,153 B1 | 1/2003 | Littek et al. |
| 6,561,986 B2 | 5/2003 | Baura et al. |
| 6,564,077 B2 | 5/2003 | Mortara |
| 6,606,511 B1 | 8/2003 | Ali et al. |
| 6,609,016 B1 | 8/2003 | Lynn |
| 6,684,090 B2 | 1/2004 | Ali et al. |
| 6,694,178 B1 | 2/2004 | Soula et al. |
| 6,702,752 B2 | 3/2004 | Dekker |
| 6,709,402 B2 | 3/2004 | Dekker |
| 6,748,252 B2 | 6/2004 | Lynn et al. |
| 6,754,516 B2 | 6/2004 | Mannheimer |
| 6,760,608 B2 | 7/2004 | Lynn |
| 6,783,498 B2 | 8/2004 | Sackner et al. |
| 6,816,741 B2 | 11/2004 | Diab |
| 6,839,581 B1 | 1/2005 | El Solh et al. |
| 6,896,661 B2 | 5/2005 | Dekker |
| 6,905,470 B2 | 6/2005 | Lee et al. |
| 6,925,324 B2 | 8/2005 | Shusterman |
| 6,931,269 B2 | 8/2005 | Terry |
| 6,966,878 B2 | 11/2005 | Schoisswohl et al. |
| 6,970,792 B1 | 11/2005 | Diab |
| 6,980,679 B2 | 12/2005 | Jeung et al. |
| 7,020,507 B2 | 3/2006 | Scharf et al. |
| 7,035,679 B2 | 4/2006 | Addison et al. |
| 7,043,293 B1 | 5/2006 | Baura |
| 7,044,918 B2 | 5/2006 | Diab |
| 7,070,566 B2 | 7/2006 | Medero et al. |
| 7,079,888 B2 | 7/2006 | Oung et al. |
| 7,147,601 B2 | 12/2006 | Marks et al. |
| 7,177,682 B2 | 2/2007 | Lovett |
| 7,190,261 B2 | 3/2007 | Al-Ali |
| 7,215,986 B2 | 5/2007 | Diab et al. |
| 7,218,966 B2 | 5/2007 | Haefner |
| 7,254,425 B2 | 8/2007 | Lowery et al. |
| 7,283,870 B2 | 10/2007 | Kaiser et al. |
| 7,336,982 B2 | 2/2008 | Yoo |
| 7,355,512 B1 | 4/2008 | Al-Ali |
| 7,367,339 B2 | 5/2008 | Bickle |
| 7,367,949 B2 | 5/2008 | Korhonen et al. |
| 7,398,115 B2 | 7/2008 | Lynn |
| 7,403,806 B2 | 7/2008 | Norris |
| 7,407,486 B2 | 8/2008 | Huiku et al. |
| 7,415,297 B2 | 8/2008 | Al-Ali et al. |
| 7,438,683 B2 | 10/2008 | Al-Ali et al. |
| 7,440,787 B2 | 10/2008 | Diab |
| 7,470,235 B2 | 12/2008 | Moriya et al. |
| 7,485,095 B2 | 2/2009 | Shusterman |
| 7,496,393 B2 | 2/2009 | Diab et al. |
| 7,499,835 B2 | 3/2009 | Weber et al. |
| 7,523,011 B2 | 4/2009 | Akiyama et al. |
| 7,561,912 B2 | 7/2009 | Schatz et al. |
| 7,610,324 B2 | 10/2009 | Troyansky et al. |
| 7,690,378 B1 | 4/2010 | Turcott |
| 7,801,591 B1 | 9/2010 | Shusterman |
| 7,869,980 B2 | 1/2011 | Casler et al. |
| 7,887,502 B2 | 2/2011 | Ross et al. |
| 7,894,868 B2 | 2/2011 | Al-Ali et al. |
| 7,899,507 B2 | 3/2011 | Al-Ali et al. |
| 7,976,472 B2 | 7/2011 | Kiani |
| 7,988,637 B2 | 8/2011 | Diab |
| 8,019,400 B2 | 9/2011 | Diab et al. |
| 8,046,040 B2 | 10/2011 | Ali et al. |
| 8,130,105 B2 | 3/2012 | Al-Ali et al. |
| 8,203,438 B2 | 6/2012 | Kiani et al. |
| 8,275,553 B2 | 9/2012 | Amundson et al. |
| 8,364,223 B2 | 1/2013 | Al-Ali et al. |
| 8,755,871 B2 | 6/2014 | Weng et al. |
| 8,880,576 B2 | 11/2014 | Ochs et al. |
| 2002/0038078 A1 | 3/2002 | Ito |
| 2002/0117173 A1 | 8/2002 | Lynn et al. |
| 2003/0036685 A1 | 2/2003 | Goodman |
| 2003/0158466 A1 | 8/2003 | Lynn |
| 2003/0163054 A1 | 8/2003 | Dekker |
| 2004/0015091 A1 | 1/2004 | Greenwald et al. |
| 2004/0225225 A1 | 11/2004 | Naumov et al. |
| 2005/0004479 A1 | 1/2005 | Townsend et al. |
| 2005/0022606 A1 | 2/2005 | Partin et al. |
| 2005/0027205 A1 | 2/2005 | Tarassenko et al. |
| 2005/0049470 A1 | 3/2005 | Terry |
| 2005/0070774 A1 | 3/2005 | Addison et al. |
| 2005/0115561 A1 | 6/2005 | Stahmann et al. |
| 2005/0222502 A1 | 10/2005 | Cooper |
| 2005/0222503 A1 | 10/2005 | Dunlop et al. |
| 2006/0122476 A1 | 6/2006 | Van Slyke |
| 2006/0192667 A1 | 8/2006 | Al-Ali |
| 2006/0211930 A1 | 9/2006 | Scharf et al. |
| 2006/0217614 A1 | 9/2006 | Takala et al. |
| 2006/0258921 A1 | 11/2006 | Addison et al. |
| 2007/0004977 A1 | 1/2007 | Norris |
| 2007/0010723 A1 | 1/2007 | Uutela et al. |
| 2007/0073120 A1 | 3/2007 | Li et al. |
| 2007/0073124 A1 | 3/2007 | Li et al. |
| 2007/0129636 A1 | 6/2007 | Friedman et al. |
| 2007/0149890 A1 | 6/2007 | Li et al. |
| 2007/0032639 A1 | 8/2007 | Baker |
| 2007/0213619 A1 | 9/2007 | Lindner |
| 2007/0213621 A1 | 9/2007 | Reisfeld et al. |
| 2007/0255146 A1 | 11/2007 | Andrews et al. |
| 2007/0293896 A1 | 12/2007 | Haefner |
| 2008/0067132 A1 | 3/2008 | Ross et al. |
| 2008/0077022 A1 | 3/2008 | Baker |
| 2008/0167540 A1 | 7/2008 | Korhonen et al. |
| 2008/0200775 A1 | 8/2008 | Lynn |
| 2008/0249382 A1 | 10/2008 | Oh et al. |
| 2008/0287815 A1 | 11/2008 | Chon et al. |
| 2009/0163784 A1 | 6/2009 | Sarpeshkar et al. |
| 2009/0247837 A1 | 10/2009 | Ochs et al. |
| 2009/0306487 A1 | 12/2009 | Crowe et al. |
| 2009/0306524 A1 | 12/2009 | Muhlsteff et al. |
| 2009/0326349 A1 | 12/2009 | McGonigle |
| 2009/0326395 A1 | 12/2009 | Watson |
| 2009/0326831 A1 | 12/2009 | McGonigle et al. |
| 2010/0081897 A1 | 4/2010 | Li et al. |
| 2010/0081899 A1 | 4/2010 | McKenna |
| 2010/0113904 A1 | 5/2010 | Batchelder et al. |
| 2010/0113908 A1 | 5/2010 | Vargas et al. |
| 2010/0113909 A1 | 5/2010 | Batchelder et al. |
| 2010/0174160 A1 | 7/2010 | Chance |
| 2010/0286495 A1 | 11/2010 | McGonigle |
| 2010/0292568 A1 | 11/2010 | Droitcour et al. |
| 2010/0324389 A1 | 12/2010 | Moon et al. |
| 2011/0021892 A1 | 1/2011 | Addison et al. |
| 2011/0066062 A1 | 3/2011 | Banet et al. |
| 2011/0071406 A1 | 3/2011 | Addison et al. |
| 2012/0232398 A1 | 9/2012 | Roham et al. |
| 2012/0253140 A1 | 10/2012 | Addison et al. |
| 2012/0296219 A1 | 11/2012 | Chon et al. |

(56) References Cited

U.S. PATENT DOCUMENTS

| | | |
|---|---|---|
| 2012/0310051 A1 | 12/2012 | Addison et al. |
| 2013/0137936 A1 | 5/2013 | Baker, Jr. et al. |
| 2013/0138002 A1 | 5/2013 | Weng et al. |
| 2013/0172767 A1 | 7/2013 | Dripps et al. |

FOREIGN PATENT DOCUMENTS

| | | | |
|---|---|---|---|
| EP | 1507474 B1 | 2/2009 | |
| WO | WO 00/21438 | 4/2000 | |
| WO | WO 03/000125 A1 | 1/2003 | |
| WO | WO 03/055395 A1 | 7/2003 | |
| WO | WO 03/084396 A1 | 10/2003 | |
| WO | WO 2004/075746 A2 | 9/2004 | |
| WO | WO 2004075746 A2 * | 9/2004 | ........... A61B 5/0002 |
| WO | WO 2008/135985 A1 | 11/2008 | |
| WO | WO 2009/043028 A2 | 4/2009 | |
| WO | WO 2010/030238 A1 | 3/2010 | |
| WO | WO 2010/135518 A1 | 11/2010 | |
| WO | WO-2012/014065 A1 | 2/2012 | |
| WO | WO 2012/051295 A2 | 4/2012 | |

OTHER PUBLICATIONS

Lesurf, Jim. "FM & PM Demodulation." Oct. 2, 2007. https://web.archive.org/web/20071002193422/http://www.st-andrews.ac.uk/~www_pa/Scots_Guide/RadCom/part13/page1.html.

International Search Report and Written Opinion of the International Searching Authority for Application No. PCT/US2013/020338, mailed on Apr. 11, 2013. 6 pages.

International Search Report and Written Opinion of the International Searching Authority for application No. PCT/US2014/014875, mailed on May 15, 2014.

Stagg and Gennser, "Electronic analysis of foetal breathing movements: A practical application of phase-locked- loop principles," Journal of Med. Eng. and Tech., Sep. 1978, vol. 2, No. 5, pp. 246-249.

Rapaport and Cousin, "New phase-lock tracking instrument for foetal breathing monitoring," Med. & Biol. Eng. & Comp. 1982, vol. 20, pp. 1-6.

Lindberg, L.G., Ughall, H., Oberg, P.A., "Monitoring of respiratory and heart rates using a fibre-optic sensor," Medical & Biological Engineering & Computing, Sep. 1992, pp. 533-537.

Addison, Paul S. et al., "Developing an Algorithm for Pulse Oximetry Derived Respiratory Rate (RRoxi): A Healthy Volunteer Study," Journal of Clinical Monitoring & Computing, 2012, 26: 45-51.

International Search Report and Written Opinion of the International Searching Authority for application No. PCT/US2014/014899, mailed on May 15, 2014.

Nguyen et al., "Comparison of two Methods for Demodulation of Pulse Signals—Application in Case of Central Sleep Apnea." Journal of Science and Technology, 49(1), 2011, pp. ISSN:0866-708X.

Supplementary European Search Report from the European Patent Office in European Patent Application No. 14749411, dated Aug. 10, 2016.

\* cited by examiner

SYSTEMS AND METHODS FOR DETERMINING RESPIRATION INFORMATION FROM A PHYSIOLOGICAL SIGNAL USING AMPLITUDE DEMODULATION

The present disclosure relates to physiological signal processing, and more particularly relates to determining respiration information from a physiological signal using amplitude demodulation.

SUMMARY

A method for determining respiration information for a patient comprises receiving a photoplethysmograph (PPG) signal that includes an amplitude modulation component caused at least in part by respiration. The PPG signal may be processed to move the amplitude modulation component into a baseline component of the PPG signal to generate a processed PPG signal. The processed PPG signal may be analyzed to determine the respiration information based on the amplitude modulation component.

A non-transitory computer-readable storage medium for use in determining respiration information for a patient has computer program instructions recorded thereon for receiving a PPG signal that includes an amplitude modulation component caused at least in part by respiration. The computer program instructions are also for processing the PPG signal to move the amplitude modulation component into a baseline component of the PPG signal to generate a processed PPG signal. The computer program instructions are also for analyzing the processed PPG signal to determine the respiration information based on the amplitude modulation component.

A patient monitoring system comprises processing equipment configured to receive a PPG signal that includes an amplitude modulation component caused at least in part by respiration. The processing equipment processes the PPG signal to move the amplitude modulation component into a baseline component of the PPG signal to generate a processed PPG signal. The processing equipment analyzes the processed PPG signal to determine the respiration information based on the amplitude modulation component.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
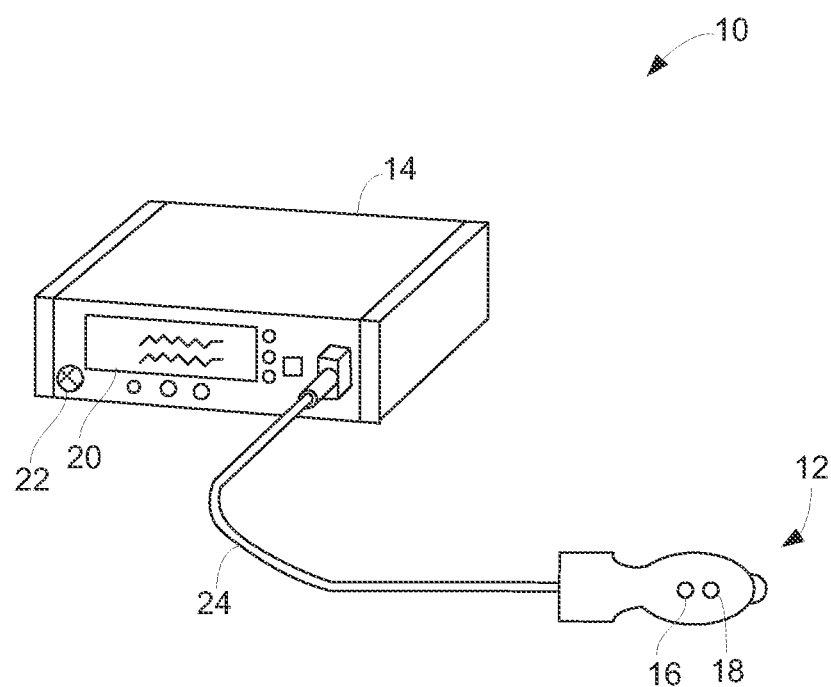
FIG. 1 shows an illustrative patient monitoring system in accordance with some embodiments of the present disclosure.

A physiological signal such as a photoplethysmograph (PPG) signal may be indicative of pulsatile blood flow. Pulsatile blood flow may be dependent on a number of physiological functions such as cardiovascular function and respiration. For example, the PPG signal may exhibit a periodic component that generally corresponds to the heart beat of a patient. This pulsatile component of the PPG signal may be used to determine physiological parameters such as heart rate.

Respiration may also impact the pulsatile blood flow that is indicated by the PPG signal. For example, respiration may cause changes in the amplitude and frequency of the PPG signal. By identifying, extracting, isolating, or otherwise utilizing the amplitude modulation component, frequency modulation component, or both of the PPG signal, it may be possible to calculate respiration information such as respiration rate from the PPG signal.

The pulsatile component of the PPG signal may provide a carrier signal for the amplitude modulation component of the PPG signal, the frequency modulation component of the PPG signal, or both. Signal analysis techniques (e.g., Fourier analysis, Hilbert transforms, and wavelet techniques) may sometimes not effectively discern the amplitude modulation component or frequency modulation component from the carrier signal, and therefore may not be able to accurately determine respiration information such as respiration rate from a conventional PPG signal.

As is described herein, the amplitude modulation component, frequency modulation component, or both, may be demodulated from the pulsatile component of the PPG signal. Demodulating the amplitude modulation component, frequency modulation component, or both, may move the respective component(s) to a baseline component of the PPG signal, such that a signal generally corresponding to respiration is discernible within the baseline component of the PPG signal. Signal analysis techniques may be utilized to determine respiration information based on the amplitude modulation component, frequency modulation component, or both.

For purposes of clarity, the present disclosure is written in the context of the physiological signal being a PPG signal generated by a pulse oximetry system. It will be understood that any other suitable physiological signal or any other suitable system may be used in accordance with the teachings of the present disclosure.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations that are not typically understood to be optimal for pulse oximetry serve as suitable sensor locations for the monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_0$=intensity of light transmitted;
S=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I=\log I_o-(s\beta_o+(1-s)\beta_r)l. \quad (2)$$

2. Eq. 2 is then differentiated with respect to time to yield $$\frac{d\log I}{dt}=-(s\beta_o+(1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{\frac{d\log I(\lambda_R)}{dt}}{\frac{d\log I(\lambda_{IR})}{dt}}=\frac{s\beta_o(\lambda_R)+(1-s)\beta_r(\lambda_R)}{s\beta_o(\lambda_{IR})+(1-s)\beta_r(\lambda_{IR})}. \quad (4)$$

4. Solving for S yields $$s=\frac{\frac{d\log I(\lambda_{IR})}{dt}\beta_r(\lambda_R)-\frac{d\log I(\lambda_R)}{dt}\beta_r(\lambda_{IR})}{\frac{d\log I(\lambda_R)}{dt}(\beta_o(\lambda_{IR})-\beta_r(\lambda_{IR}))-\frac{d\log I(\lambda_{IR})}{dt}(\beta_o(\lambda_R)-\beta_r(\lambda_R))}. \quad (5)$$

5. Note that, in discrete time, the following approximation can be made:

$$\frac{d\log I(\lambda,t)}{dt}\simeq \log I(\lambda,t_2)-\log I(\lambda,t_1). \quad (6)$$

6. Rewriting Eq. 6 by observing that log A−log B=log(A/B) yields $$\frac{d\log I(\lambda,t)}{dt}\simeq \log\left(\frac{I(t_2,\lambda)}{I(t_1,\lambda)}\right). \quad (7)$$

7. Thus, Eq. 4 can be expressed as $$\frac{\frac{d\log I(\lambda_R)}{dt}}{\frac{d\log I(\lambda_{IR})}{dt}}\simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)}=R, \quad (8)$$

where R represents the "ratio of ratios."

8. Solving Eq. 4 for S using the relationship of Eq. 5 yields $$s=\frac{\beta_r(\lambda_R)-R\beta_r(\lambda_{IR})}{R(\beta_o(\lambda_{IR})-\beta_r(\lambda_{IR}))-\beta_o(\lambda_R)+\beta_r(\lambda_R)}. \quad (9)$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{\frac{dI}{dt}}{I}, \quad (10)$$

Eq. 8 becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} = \quad (11)$$

$$\frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)} = R,$$

which defines a cluster of points whose slope of y versus x will give R when $$x = [I(t_2, \lambda_{IR}) - I(t_1, \lambda_{IR})]I(t_1, \lambda_R), \quad (12)$$

and $$y = [I(t_2, \lambda_R) - I(t_1, \lambda_R)]I(t_1, \lambda_{IR}). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

FIG. 1 is a perspective view of an embodiment of a patient monitoring system 10. System 10 may include sensor unit 12 and monitor 14. In some embodiments, sensor unit 12 may be part of an oximeter. Sensor unit 12 may include an emitter 16 for emitting light at one or more wavelengths into a patient's tissue. A detector 18 may also be provided in sensor unit 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a patient's forehead, while a second sensor unit may be positioned at a patient's fingertip.

Sensor units may each detect any signal that carries information about a patient's physiological state, such as an electrocardiograph signal, arterial line measurements, or the pulsatile force exerted on the walls of an artery using, for example, oscillometric methods with a piezoelectric transducer. According to some embodiments, system 10 may include two or more sensors forming a sensor array in lieu of either or both of the sensor units. Each of the sensors of a sensor array may be a complementary metal oxide semiconductor (CMOS) sensor. Alternatively, each sensor of an array may be charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In some embodiments, emitter 16 and detector 18 may be arranged so that light from emitter 16 penetrates the tissue and is reflected by the tissue into detector 18, such as in a sensor designed to obtain pulse oximetry data from a patient's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood oxygen saturation (e.g., $SpO_2$), and respiration information) based at least in part on data relating to light emission and detection received from one or more sensor units such as sensor unit 12 and an additional sensor (not shown). In some embodiments, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may allow communication between monitor 14 and sensor unit 12.

As is described herein, monitor 14 may generate a PPG signal based on the signal received from sensor unit 12. The PPG signal may consist of data points that represent a pulsatile waveform. The pulsatile waveform may be modulated based on the respiration of a patient. Respiratory modulations may include baseline modulations, amplitude modulations, frequency modulations, respiratory sinus arrhythmia, any other suitable modulations, or any combination thereof. Respiratory modulations may exhibit different phases, amplitudes, or both, within a PPG signal and may contribute to complex behavior (e.g., changes) of the PPG signal. For example, the amplitude of the pulsatile waveform may be modulated based on respiration (amplitude modulation), the frequency of the pulsatile waveform may be modulated based on respiration (frequency modulation), and a signal baseline for the pulsatile waveform may be modulated based on respiration (baseline modulation). Monitor 14 may analyze the PPG signal (e.g., by demodulating the PPG signal) to determine respiration information based on one or more of these modulations of the PPG signal.

As is described herein, respiration information may be determined from the PPG signal by monitor 14. However, it will be understood that the PPG signal could be transmitted to any suitable device for the determination of respiration information, such as a local computer, a remote computer, a nurse station, mobile devices, tablet computers, or any other device capable of sending and receiving data and performing processing operations. Information may be transmitted from monitor 14 in any suitable manner, including wireless (e.g., WiFi, Bluetooth, etc.), wired (e.g., USB, Ethernet, etc.), or application-specific connections. The receiving device may determine respiration information as described herein.

Figure 2:
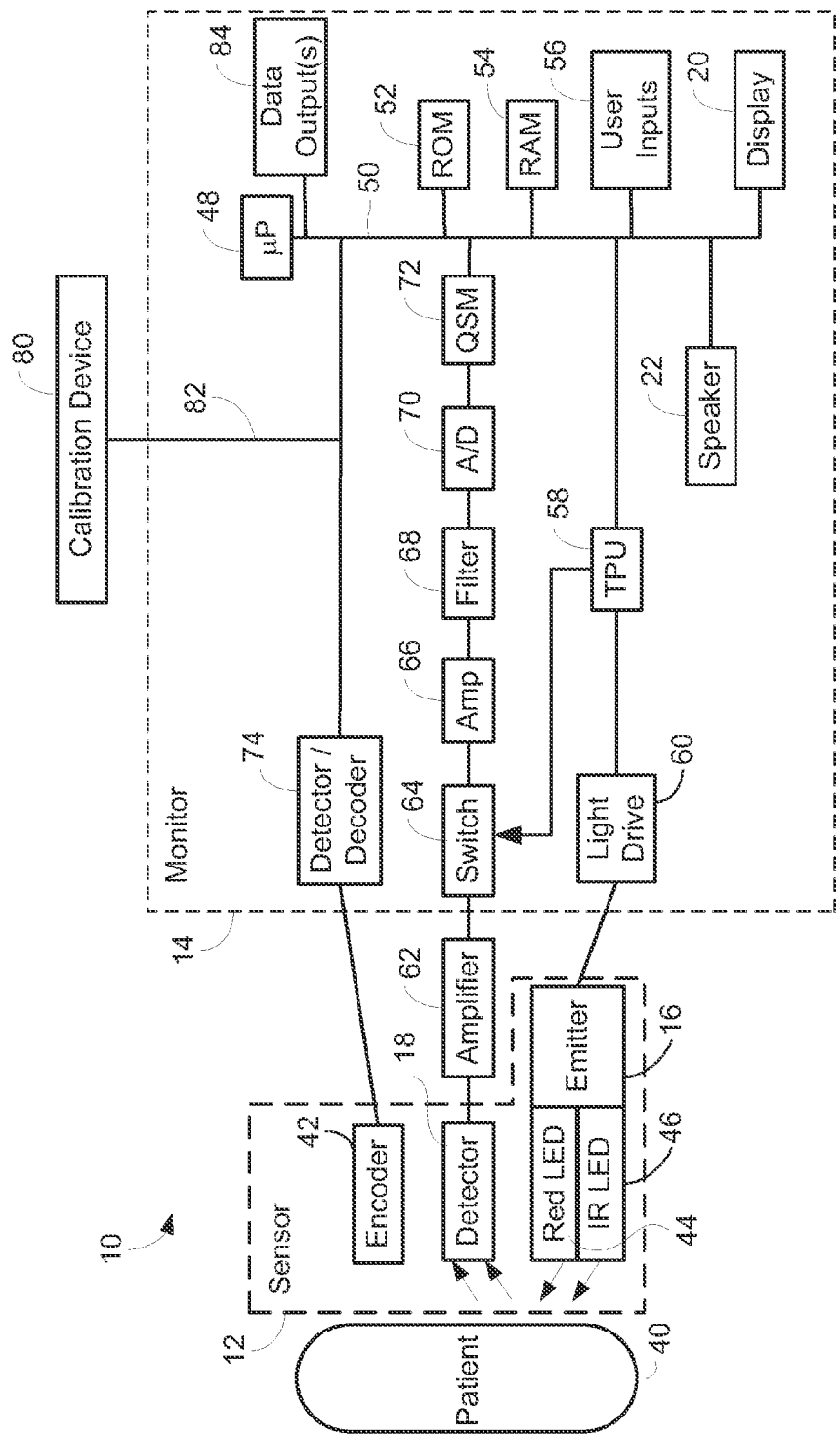
FIG. 2 is a block diagram of the illustrative patient monitoring system of FIG. 1 coupled to a patient in accordance with some embodiments of the present disclosure.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor may emit only a Red light while a second sensor may emit only an IR light. In a further example, the wavelengths of light used may be selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In some embodiments, encoder 42 may contain information about sensor unit 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which measurements may be determined based at least in part on the signal or signals received at sensor unit 12. For example, some pulse oximetry sensors rely on equations to relate an area under a portion of a PPG signal corresponding to a physiological pulse to determine blood pressure. These equations may contain coefficients that depend upon a patient's physiological characteristics as stored in encoder 42.

Encoder 42 may, for instance, be a coded resistor that stores values corresponding to the type of sensor unit 12 or the type of each sensor in the sensor array, the wavelengths of light emitted by emitter 16 on each sensor of the sensor array, and/or the patient's characteristics and treatment information. In some embodiments, encoder 42 may include a memory on which one or more of the following information may be stored for communication to monitor 14; the type of the sensor unit 12; the wavelengths of light emitted by emitter 16; the particular wavelength each sensor in the sensor array is monitoring; a signal threshold for each sensor in the sensor array; any other suitable information; physiological characteristics (e.g., gender, age, weight); or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, data output 84, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data.

Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In some embodiments, microprocessor 48 may determine the patient's physiological parameters, such as $SpO_2$, pulse rate, and/or respiration information, using various algorithms and/or look-up tables based on the value of the received signals and/or data corresponding to the light received by detector 18. As is described herein, microprocessor 48 may utilize amplitude demodulation and/or frequency demodulation techniques to determine respiration information from a PPG signal.

Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable microprocessor 48 to determine the thresholds based at least in part on algorithms or look-up tables stored in ROM 52. In some embodiments, user inputs 56 may be used to enter information, select one or more options, provide a response, input settings, any other suitable inputting function, or any combination thereof. User inputs 56 may be used to enter information about the patient, such as age, weight, height, diagnosis, medications, treatments, and so forth. In some embodiments, display 20 may exhibit a list of values, which may generally apply to the patient, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Data output 84 may provide for communications with other devices utilizing any suitable transmission medium, including wireless (e.g., WiFi, Bluetooth, etc.), wired (e.g., USB, Ethernet, etc.), or application-specific connections. Data output 84 may receive messages to be transmitted from microprocessor 48 via bus 50. Exemplary messages to be sent in an embodiment described herein may include samples of the PPG signal to be transmitted to an external device for determining respiration information.

The optical signal attenuated by the tissue of patient 40 can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. Also, because blood is a fluid, it responds differently than the surrounding tissue to inertial effects, which may result in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals, control the amount of noise present in the signal, or otherwise identify noise components in order to prevent them from affecting measurements of physiological parameters derived from the sensor signals.

Figure 3:
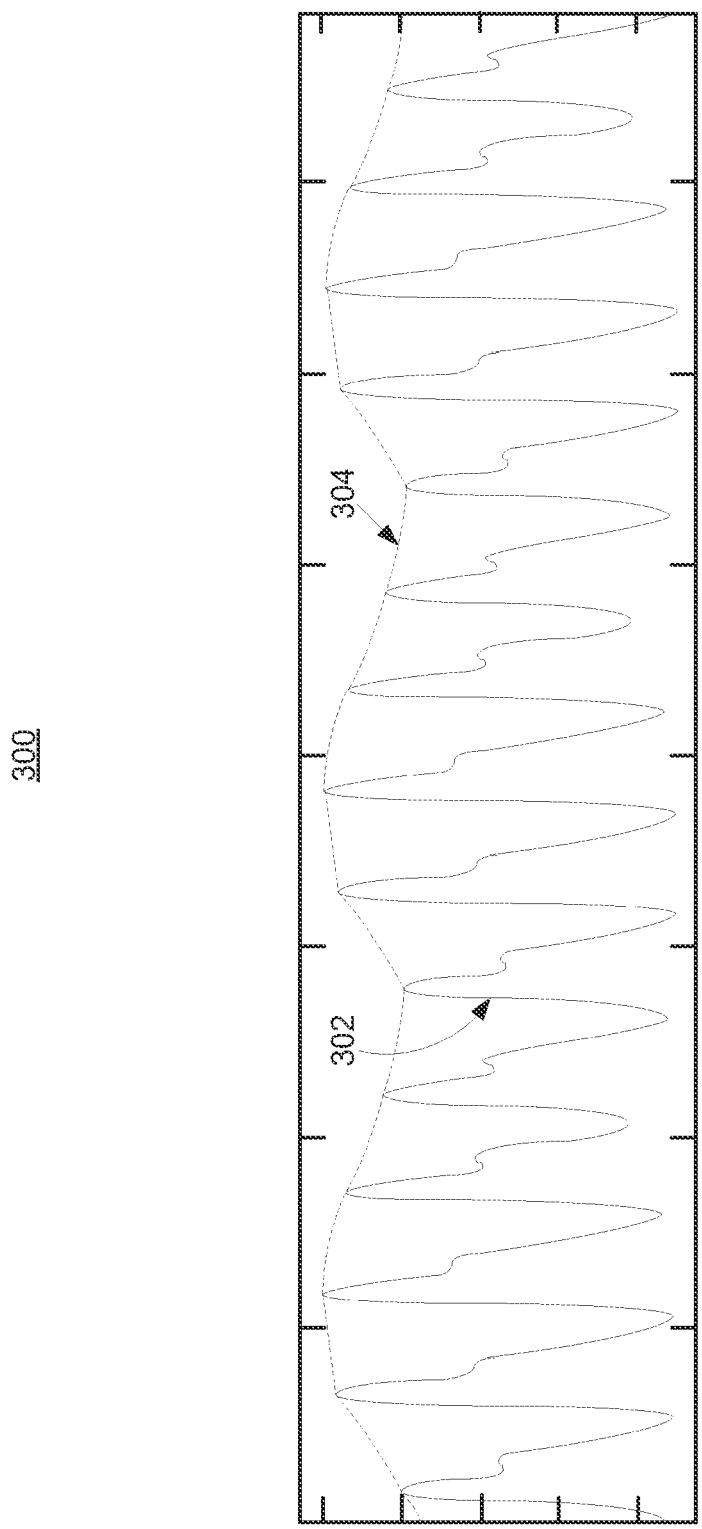
FIG. 3 shows an illustrative amplitude modulated PPG signal in accordance with some embodiments of the present disclosure.

FIG. 3 shows an illustrative amplitude modulated PPG signal in accordance with some embodiments of the present disclosure. A PPG signal may demonstrate multiple modulations based on the respiration of a patient, such as amplitude modulation, frequency modulation, and baseline modulation. FIG. 3 depicts a PPG signal including at least an amplitude modulation component of the PPG signal due to respiration. PPG signal 302 may be a periodic signal that is indicative of changes in pulsatile blood flow. Each cycle of PPG signal 302 may generally correspond to pulse, such that a heart rate may be determined based on PPG signal 302.

The volume of the pulsatile blood flow may also vary in a periodic manner based on respiration. The period of a respiratory cycle may typically be longer than the period of a pulsatile cycle, such that any changes in the pulsatile blood flow due to respiration occur over a number of pulsatile cycles. As one example of changes in pulsatile blood flow due to respiration, the amplitude of PPG signal 302 may be modulated based on respiration. In the exemplary embodiment depicted in FIG. 3, the peak-to-peak amplitude of the pulsatile blood flow depicted by PPG signal 302 may vary based on a respiratory cycle caused by an amplitude modulation component 304.

Although it will be understood that the respiratory amplitude modulation component 304 may impact the amplitude of PPG signal 302 differently based on patient conditions, measurement location, or other factors, in the exemplary embodiment of FIG. 3, the peak-to-peak amplitude of PPG signal 302 varies in a generally uniform manner based on a respiratory cycle. Each cycle of respiratory amplitude modulation component 304 may correspond to a breath. For example, as is depicted in FIG. 3 a single breath may occur approximately once for every five pulsatile cycles (e.g., heart beats). Accordingly, a respiration rate corresponding to respiratory amplitude modulation component 304 may be approximately one fifth of the pulse rate associated with PPG signal 302. As will be described herein, respiration rate may be determined by isolating, extracting, or otherwise identifying the amplitude modulation component 304 of PPG signal 302.

Figure 4:
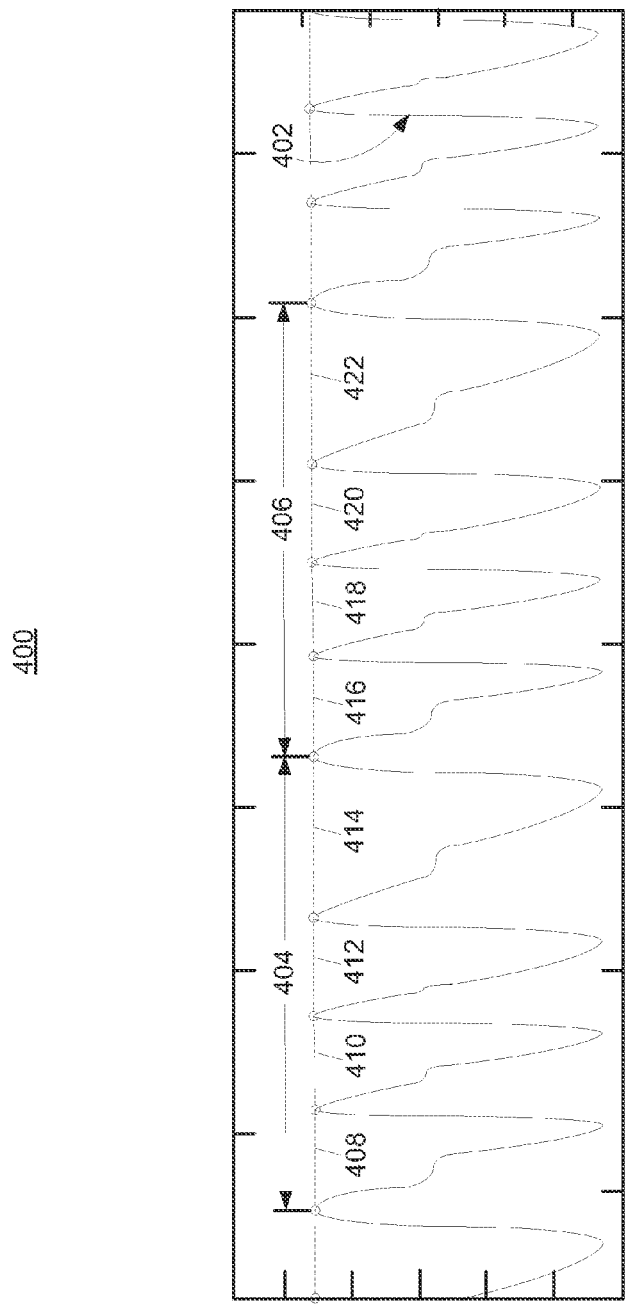
FIG. 4 shows an illustrative frequency modulated PPG signal in accordance with some embodiments of the present disclosure.

FIG. 4 shows an illustrative frequency modulated PPG signal in accordance with some embodiments of the present disclosure. FIG. 4 depicts a PPG signal 402 including at least a frequency modulation component of the PPG signal due to respiration. PPG signal 402 may be a periodic signal that is indicative of changes in pulsatile blood flow. Each cycle of PPG signal 402 may generally correspond to pulse, such that a heart rate may be determined based on the frequency of PPG signal 402.

The timing of the pulsatile blood flow may vary in a periodic manner based on respiration. The period of a respiratory cycle may typically be longer than the period of a pulsatile cycle, such that any changes in the pulsatile blood flow due to respiration occur over a number of pulsatile cycles. As one example of changes in pulsatile blood flow due to respiration, The phase and frequency of PPG signal 402 may be modulated based on respiration. In the exemplary embodiment depicted in FIG. 4, the timing, frequency, and period associated with each pulsatile cycle may vary based on a frequency modulation component (e.g., 404, 406) associated with the respiratory cycle.

In an exemplary embodiment, a series of pulses may have a relatively uniform pulse period in the absence of frequency modulation (not depicted). Although it will be understood that the frequency modulation of PPG signal 402 may impact the phase and frequency of PPG signal 402 differently based on patient conditions, measurement location, etc., in the exemplary embodiment of FIG. 4 the pulse period associated with individual pulses may vary in a generally uniform manner based on the relative timing of pulses within a respiratory cycle. For example, respiratory cycles 404 and 406 may each correspond to a breath of a patient, and a respiration rate at approximately one fourth of the pulse rate. The pulsatile flow of PPG signal 402 may vary such that the period of each pulse is altered based on the relative location within the respiratory cycle, as depicted by pulse periods 408, 410, 412, 414, 416, 418, 420, and 422. As will be described herein, respiration information such as a respiration rate may be determined by isolating, extracting, or otherwise identifying the respiratory frequency modulation component (e.g., 404, 406) of PPG signal 402.

Figure 5:
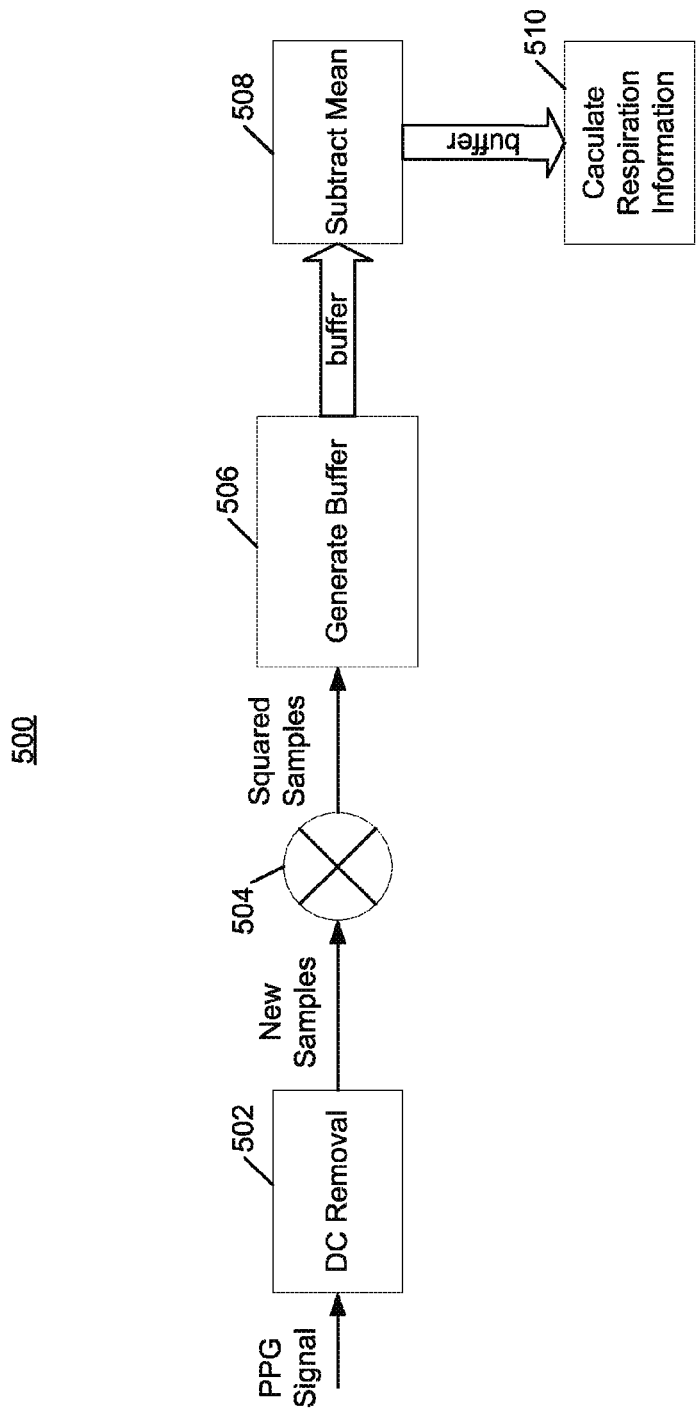
FIG. 5 is a flow diagram showing an illustrative flow for determining respiration information based on amplitude demodulation of a physiological signal in accordance with some embodiments of the present disclosure.

FIG. 5 is a signal flow diagram showing illustrative signal processing blocks for determining respiration information based on an amplitude demodulation component of a PPG signal in accordance with some embodiments of the present disclosure. Although in an exemplary embodiment, the steps may be performed as depicted in FIG. 5, it will be understood that the order of the steps may be modified, steps may be omitted, or additional steps may be added. Although in an exemplary embodiment respiration information may be determined by monitor 14, it will be understood that respiration information may be determined by any suitable processing equipment, such as a remote computer, docking station, nurse station, tablet device, or smart phone. For example, monitor 14 may transmit a signal having samples of a PPG signal to a remote computer, and the remote computer may determine respiration information from the PPG signal. In other embodiments, some of the operations depicted in FIG. 5 may be performed by monitor 14 while other operations may be performed by other processing equipment.

In an exemplary embodiment, monitor 14 may generate, receive, or otherwise acquire a PPG signal as described herein. Signal processing operations may be performed to allow an amplitude modulation component of the PPG signal to be more readily identified to determine respiration information. Although the amplitude modulation component of the PPG signal may be processed in any suitable manner, in an exemplary embodiment, the amplitude modulation component of the PPG signal may be moved to a baseline component of the PPG signal.

At step 502, monitor 14 may remove a DC component, signal components below an expected breathing band, or both, from the PPG signal. DC removal may be performed in any suitable manner, including filtering the PPG signal (e.g., a high-pass or band-pass filter) or identifying and removing (e.g., by subtracting) the DC component of the signal. Although a DC component of the PPG signal may be identified for removal in any suitable manner, in exemplary embodiments, the DC component may be identified based on calculating an average value of the PPG signal, a mean value of the PPG signal or of individual pulses within a PPG signal, a median value of the PPG signal or of individual pulses of the PPG signal, or based on any other suitable mathematical or statistical operations. In an exemplary embodiment, the DC component of the signal may be identified by curve fitting of any suitable order (e.g., a second order curve fit). Once a value associated with a DC component of the PPG signal is calculated, the DC component may be removed in any suitable manner, such as subtracting the DC component from the PPG signal baseline (e.g., on a sample by sample basis). A set of new samples of the PPG signal may be generated based on DC removal.

At step 504, signal processing operations may be performed to generate a processed PPG signal for identifying an amplitude modulation component of the PPG signal. As will be described herein, respiration information may be more readily identified by moving the amplitude modulation component of the PPG signal to the baseline component of the PPG signal, for example, based on a identifying the amplitude modulation component within an expected range of respiration rates.

Although the processed PPG signal may be generated in any suitable manner, in an exemplary embodiment, each of the new samples of the PPG signal may be squared by a multiplier. The periodic pulsatile component of the PPG signal has a pulse rate and may act as a carrier for the amplitude modulation component of the PPG signal based on the frequency associated with the pulse rate. The PPG signal (e.g., as represented by the new samples) may be represented as a carrier signal at the pulsatile frequency with sidebands based on the frequency associated with the amplitude modulation component. It will be understood that squaring the samples partially rectifies the PPG signal, resulting in multiple signal components including a DC component, harmonics of the carrier and sidebands, and the desired amplitude modulation component of the PPG signal (i.e., demodulated to a baseline component of the PPG signal from the carrier).

At step 506, a data buffer corresponding to a window of data of the processed PPG signal may be generated from the squared samples. Although it will be understood that any suitable window of data may be used, in an exemplary embodiment the window of data may include 30 seconds of the data from the processed PPG signal. At step 508, the mean amplitude of the samples in the buffer may be determined and subtracted from each sample in the buffer.

At step 510, respiration information may be calculated for the buffer data of the processed PPG signal. In an exemplary embodiment, the amplitude modulation component of the processed PPG signal may exhibit periodic characteristics based on respiration. In an exemplary embodiment, a Hilbert transform may be performed on the buffer data and the respiration information may be identified within a region of interest for respiration. In an exemplary embodiment, a Fourier transform may be performed and a frequency corresponding to the respiration information may be identified within a region of interest for respiration. In an exemplary embodiment, described herein with respect to FIG. 8, a wavelet transform may be performed on the data, a sum scalogram may be generated, and a scale associated with the respiration information may be identified.

Figure 6:
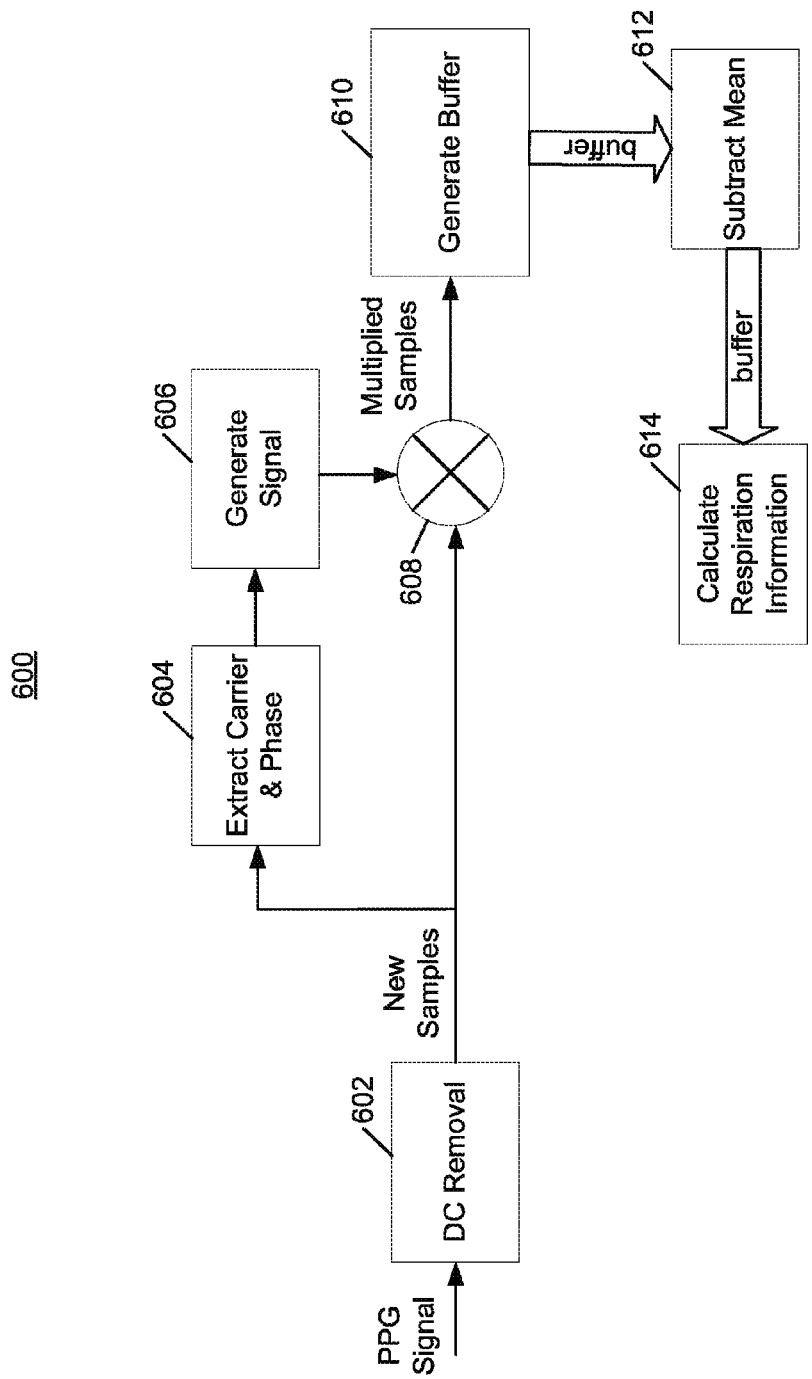
FIG. 6 is a flow diagram showing an illustrative flow for determining respiration information based on amplitude demodulation of a physiological signal in accordance with some embodiments of the present disclosure.

FIG. 6 is a flow diagram showing illustrative steps for determining respiration information based on amplitude demodulation of a PPG signal in accordance with some embodiments of the present disclosure. Although in an exemplary embodiment, the steps may be performed as depicted in FIG. 6, it will be understood that the order of the steps may be modified, steps may be omitted, or additional steps may be added. Although in an exemplary embodiment, respiration information may be determined by monitor 14, it will be understood that respiration information may be determined by any suitable processing equipment, such as a remote computer, docking station, nurse station, tablet device, or smart phone. For example, monitor 14 may transmit a signal having samples of a PPG signal to a remote computer, and the remote computer may determine respiration information from the PPG signal. In other embodiments, some of the operations depicted in FIG. 6 may be performed by monitor 14 while other operations may be performed by other processing equipment.

In an exemplary embodiment, monitor 14 may generate, receive, or otherwise acquire a PPG signal as described herein. At step 602, monitor 14 may remove a DC component, signal components below an expected breathing band, or both, from the PPG signal. DC removal may be performed in any suitable manner, including filtering the PPG signal (e.g., a high-pass or band-pass filter) or identifying and removing (e.g., by subtracting) the DC component of the signal. Although a DC component of the PPG signal may be identified for removal in any suitable manner, in exemplary embodiments the DC component may be identified based on calculating an average value of the PPG signal, a mean value of the PPG signal or of individual pulses within a PPG signal, a median value of the PPG signal or of individual pulses of the PPG signal, or based on any other suitable mathematical or statistical operations. In another exemplary embodiment the DC component of the signal may be identified by curve fitting of any suitable order (e.g., a second order curve fit). Once a value associated with a DC component of the PPG signal is calculated, the DC component may be removed in any suitable manner, such as subtracting the DC component from the entire PPG signal (e.g., on a sample by sample basis). A set of new samples of the PPG signal may be generated based on DC removal.

At step 604, signal processing operations may be performed to identify the frequency and phase of the carrier component of the PPG signal (e.g., based on the pulsatile component of the PPG signal). Although the frequency and phase of the pulsatile carrier component of the PPG signal may be identified in any suitable manner, in an exemplary embodiment a phase locked loop may determine the frequency and phase. The phase locked loop may be implemented in any suitable manner, including as software, hardware, or a combination of hardware and software.

A matched signal may be generated at step 606 based on the frequency and phase that corresponds to the pulsatile component of the PPG signal. Although the matched signal may be any suitable signal and may be generated in any suitable manner, in an exemplary embodiment a sinusoidal signal having a frequency and phase that correspond to the pulsatile component of the PPG signal may be generated. In other embodiments, a signal may be generated that generally matches the characteristics of a typical PPG signal, such as waveform shape and duty cycle. The matched signal may be generated in a manner such that samples of the matched signal correspond to the new samples generated in step 602. The matched signal may be generated in any suitable manner, including with software (e.g., operating on microprocessor 48), hardware (e.g., an integrated circuit and/or oscillator), or a combination of software and hardware.

At step 608, the matched signal may be mixed with the new samples of the PPG signal to generate a processed PPG signal for moving an amplitude modulation component of the PPG signal to a baseline component of the PPG signal. Although the processed PPG signal may be generated in any suitable manner, in an exemplary embodiment the new samples of the PPG signal and the matched signals may be input to a mixer. The periodic pulsatile component of the PPG signal may have a frequency and may act as a carrier for the amplitude modulation component of the PPG signal. The PPG signal (as represented by the new samples) may be represented as a carrier signal at the pulsatile frequency with sidebands based on the frequency associated with the amplitude modulation component. It will be understood that mixing the new samples of the PPG signal with a matched signal results in multiple signal components including harmonics of the carrier and the desired amplitude modulation component of the PPG signal (i.e., demodulated to a baseline component of the PPG signal from the carrier).

At step 610, a data buffer corresponding to a window of data of the processed PPG signal may be generated from the processed PPG signal. Respiration information may be determined from an amplitude modulation component of the PPG signal for a window of data. Although it will be understood that any suitable window of data may be used, in an exemplary embodiment the window of data may include 30 seconds of the data from the processed PPG signal. At step 612 the mean amplitude of the buffer may be determined and subtracted from each sample in the buffer.

At step 614, respiration information may be calculated for the buffer data of the processed PPG signal. Although it will be understood that respiration information (e.g., respiration rate) may be determined based on the amplitude modulation component of the processed PPG signal in any suitable manner, in an exemplary embodiment, the amplitude modulation component may exhibit periodic characteristics based on respiration rate. In an exemplary embodiment, a Hilbert transform may be performed on the buffer data and the respiration information may be identified within a region of interest for respiration. In another exemplary embodiment, a Fourier transform may be performed and a frequency corresponding to the respiration information may be identified within a region of interest for respiration. In another exemplary embodiment, described herein with respect to FIG. 8, a wavelet transform may be performed on the data, a sum scalogram may be generated, and a scale associated with the respiration information may be identified.

Figure 7:
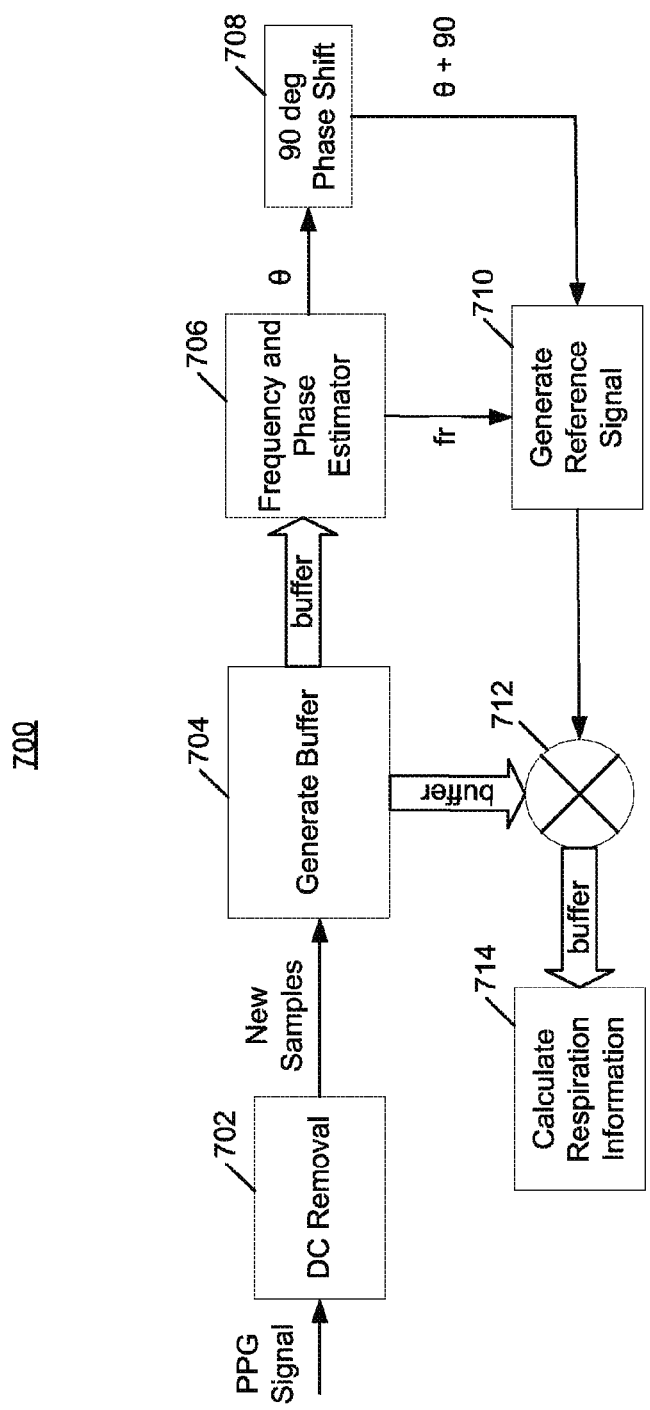
FIG. 7 is a flow diagram showing an illustrative flow for determining respiration information based on frequency demodulation of a physiological signal in accordance with some embodiments of the present disclosure.

FIG. 7 is a flow diagram showing illustrative signal processing blocks for determining respiration information based on frequency demodulation of a physiological signal in accordance with some embodiments of the present disclosure. Although in an exemplary embodiment the steps may be performed as depicted in FIG. 7, it will be understood that the order of the steps may be modified, steps may be omitted, or additional steps may be added. Although in an exemplary embodiment respiration information may be determined by monitor 14, it will be understood that respiration information may be determined by any suitable processing equipment, such as a remote computer, docking station, nurse station, tablet device, or smart phone. For example, monitor 14 may transmit a signal having samples of a PPG signal to a remote computer, and the remote computer may determine respiration information from the PPG signal. In other embodiments, some of the operations depicted in FIG. 7 may be performed by monitor 14 while other operations may be performed by other processing equipment.

In an exemplary embodiment, monitor 14 may generate, receive, or otherwise acquire a PPG signal as described herein. The frequency demodulation described herein may move the frequency modulation component of the PPG signal to a baseline component of the PPG signal. Signal processing operations may be performed to allow the frequency modulation component of the PPG signal to be more readily identified. For example, at step 702 monitor 14 may remove a DC component, signal components below an expected breathing band, or both, from the PPG signal. DC removal may be performed in any suitable manner, including filtering the PPG signal (e.g., a high-pass or band-pass filter) or identifying and removing (e.g., by subtracting) the DC component of the signal. Although a DC component of the PPG signal may be identified for removal in any suitable manner, in exemplary embodiments the DC component may be identified based on calculating an average value of the PPG signal, a mean value of the PPG signal or of individual pulses within a PPG signal, a median value of the PPG signal or of individual pulses of the PPG signal, or based on any other suitable mathematical or statistical operations. In another exemplary embodiment the DC component of the signal may be identified by curve fitting of any suitable order (e.g., a second order curve fit). Once a value associated with a DC component of the PPG signal is calculated, the DC component may be removed in any suitable, such as subtracting the DC component from the entire PPG signal (e.g., on a sample by sample basis). A set of new samples of the PPG signal may be generated based on DC removal.

At step 704, a window of data (buffer data) may be established for determining respiration information from a frequency modulation component of the PPG signal. Although it will be understood that any suitable window of data may be used, in an exemplary embodiment the window of data may include 30 seconds of the new samples of the PPG signal. The resulting buffer data may be provided to a mixer (step 712) and to estimate the frequency and phase of the pulsatile (carrier) component of the signal represented by the buffer data at step 706. As will be described herein, steps 706-710 may result in a reference signal (e.g., a sine wave) having the same frequency as the PPG signal (represented by the buffer data) and a predetermined phase difference (e.g., a 90° lag) with the PPG signal (represented by the buffer data). The reference signal may be mixed with the signal represented by the buffer data by mixer 712. It will be understood that this exemplary frequency demodulation technique may result in moving the frequency modulation component of the PPG signal to a baseband component of the PPG signal. It will also be understood that any suitable frequency demodulation technique may be used to move the frequency modulation component of the PPG signal to a baseline component of the PPG signal, such as phase locked loop based techniques (e.g., based on an error between the pulsatile carrier frequency and the PPG signal), a Foster-Seeley discriminator, a ratio detector, or application-specific integrated circuits.

At step 706, signal processing operations may be performed to identify a frequency and phase of the PPG signal, which may generally correspond to the carrier component of the PPG signal (e.g., the pulsatile component of the PPG signal). Although the frequency and phase of the pulsatile carrier component of the PPG signal may be identified in any suitable manner, in an exemplary embodiment a phase locked loop may extract the frequency and phase. The phase locked loop may be implemented in any suitable manner, including as software, hardware, or a combination of hardware and software. The resulting frequency information may be provided to generate a reference signal at step 710, while the phase information may be shifted based on a phase shift value at step 708.

At step 708 the phase determined at step 706 may be phase shifted in a manner that allows the frequency modulation component of the PPG signal to be demodulated from the pulsatile component of the PPG signal. Although the determined phase from step 706 may be shifted in any suitable manner, in an exemplary embodiment the phase may be shifted to have a lag of 90° from the phase of the PPG signal.

At step 710 a reference signal may be generated having a frequency that corresponds to the pulsatile component of the PPG signal (i.e., as determined at step 706) and a phase based on the phase of the pulsatile component of the PPG signal and shifted as described herein (i.e., based on the phase shift of step 708). Although the reference signal may be any suitable signal and may be generated in any suitable manner, in an exemplary embodiment the reference signal may be a sinusoidal signal that corresponds to the pulsatile component of the PPG signal as described herein. In other embodiments, a signal may be generated that generally matches the characteristics of a typical PPG signal, such as waveform shape and duty cycle. The reference signal may be generated in a manner such that samples of the reference signal correspond to the new samples generated in step 702. The reference signal may be generated in any suitable manner, including with software (e.g., operating on microprocessor 48), hardware (e.g., an integrated circuit and/or oscillator), or a combination of software and hardware.

At step 712 the reference signal may be mixed with the buffer data to generate a processed PPG signal for moving a frequency modulation component of the PPG signal to a baseline component of the PPG signal. Although the processed PPG signal may be generated in any suitable manner, in an exemplary embodiment the buffer data and the reference signal may be input to a mixer. It will be understood that mixing a signal including a modulated signal at a carrier frequency (e.g., the new samples of the PPG signal) with a second signal at the carrier frequency and having a shifted phase (e.g., the reference signal) may demodulate the frequency modulation component of the PPG signal to a baseline component of the PPG signal. The resulting mixed signal may be output as a buffer of mixed samples. As will be described herein, respiration information may be more readily identified by moving the frequency modulation component of the PPG signal to the baseline component of the PPG signal, for example, based on a identifying the frequency modulation component within an expected range of respiration rates.

At step 714 respiration information may be calculated from the buffer of mixed signal data. Based on the steps described herein, the frequency modulation component of the PPG signal may be identified within the buffer data and used to determine respiration information. Although it will be understood that respiration information may be determined from the frequency modulation component in any suitable manner, in an exemplary embodiment the frequency modulation component may exhibit periodic characteristics based on respiration rate. In an exemplary embodiment, a Hilbert transform may be performed on the buffer data and the respiration rate may be identified within a region of interest for respiration. In another exemplary embodiment, a Fourier transform may be performed and a frequency corresponding to the respiration rate may be identified within a region of interest for respiration. In another exemplary embodiment, described herein with respect to FIG. 8, a wavelet transform may be performed on the data, a sum scalogram may be generated, and a scale associated with the respiration rate may be identified.

Figure 8:
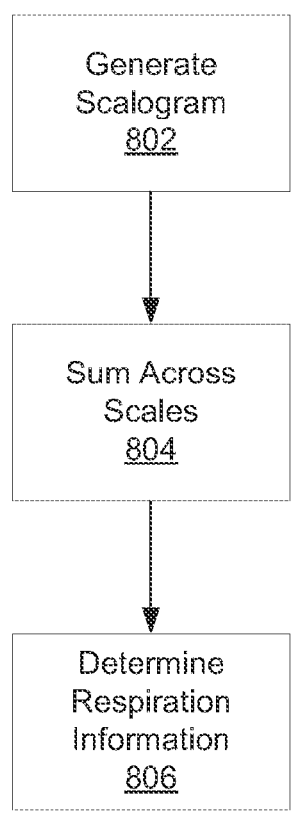
FIG. 8 is a flow diagram showing illustrative steps for determining respiration information from a scalogram in accordance with some embodiments of the present disclosure.

FIG. 8 is a flow diagram showing illustrative steps for determining respiration information from a scalogram in accordance with some embodiments of the present disclosure. Although in an exemplary embodiment the steps may be performed as depicted in FIG. 8, it will be understood that the order of the steps may be modified, steps may be omitted, or additional steps may be added. Although in an exemplary embodiment respiration information may be determined by monitor 14, it will be understood that respiration information may be determined by any suitable processing equipment, such as a remote computer, docking station, nurse station, tablet device, or smart phone. For example, monitor 14 may generate a processed PPG signal having an amplitude modulation component of a PPG signal and/or a frequency modulation component of the PPG signal moved to a baseline component of the PPG signal. The resulting signal may be transmitted to a remote computer, and the remote computer may determine respiration information from the PPG signal. In other embodiments, some of the operations depicted in FIG. 8 may be performed by monitor 14 while other operations may be performed by other processing equipment.

At step 802 a scalogram may be generated from the processed PPG signal. In one exemplary embodiment, a wavelet transform may be used to generate the scalogram. Although a number of wavelet parameters may be utilized to derive respiration information from the combined autocorrelation sequence, exemplary parameters are described below. An exemplary wavelet transform method may be a continuous wavelet transform and an exemplary wavelet may be a real Morlet wavelet. Scale parameters may be selected in any manner that captures respiration information. For example, a characteristic frequency range may be selected based on a range of frequency for respiration, such as 0.05 Hz (3 breaths per minute) to 1.0 Hz (60 breaths per minute).

At step 804, the scalogram may be summed across all scales. Although the scalogram may be summed in any suitable manner, in an exemplary embodiment each summed scale value may be calculated as a summation of all of the scale values associated with each scale. This process may be repeated for all of the scales of the scalogram, or for a subset of scales that correspond to a range of interest for respiration information.

At step 806, respiration information may be determined based on the summed scale values. In exemplary embodiments, a scale may be identified within a range of interest for respiration based on a maximum summed scale value, a predetermined pattern of summed scale values (e.g., based on a series of localized summed scale values), a set of empirical rules (e.g., based on expected respiration rate ranges, patient characteristics, etc.), or in any other suitable manner. Once a scale is identified, respiration information such as respiration rate may be calculated from the selected scale. In the exemplary embodiment described above the scales may correspond to the characteristic frequency of the corresponding wavelets, e.g., a characteristic frequency range of 0.05 Hz-1.0 Hz. Respiration information such as a respiration rate may be determined based on where the scale falls within the frequency range.

A number of exemplary techniques have been described herein for moving a amplitude modulation component of the PPG signal to a baseline component of the PPG signal, moving a frequency modulation component of the PPG signal to a baseline component of the PPG signal, and calculating respiration information from the amplitude modulation component and/or the frequency modulation component. It will be understood that any of these techniques may be combined in any suitable manner to determine respiration information. For example, both an amplitude modulation component and a frequency modulation component may be moved to a baseline component of a PPG signal. In addition, multiple techniques may be utilized demodulate each of the amplitude modulation component or frequency modulation components. Accordingly, multiple amplitude modulation components, multiple frequency modulation components, or both, may be separately processed for determination of respiration information.

These multiple modulation components may be combined in any suitable manner to determine the respiration information. Although multiple modulation components may be combined in any suitable manner, in an exemplary embodiment, a confidence value may be calculated for each modulation component. A confidence value may be calculated in any suitable manner, for example, based on the periodicity or signal strength associated with each of the amplitude modulation components or frequency modulation components.

The multiple modulation components may be combined at any suitable stage in the processing operations described herein. In an exemplary embodiment, each modulation component may be scaled based on its associated confidence value, and all of the modulation components may be combined to generate a combined modulation component. The respiration information may be calculated based on the combined modulation component. In another exemplary embodiment, the respiration information may be determined for each of the modulation components as described herein. The resulting respiration information values (e.g., respiration rate values) may be scaled based on the associated confidence values, and a combined respiration information value may be calculated by combining the scaled respiration information values.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A method for determining respiration rate for a patient, the method comprising:

receiving a photoplethysmograph (PPG) signal from a pulse oximetry sensor that is configured to photoelectrically sense absorption of light in tissue of the patient, wherein the PPG signal includes an amplitude modulation component caused at least in part by respiration;

processing, using a processor, the PPG signal to move the amplitude modulation component into a baseline component of the PPG signal to generate a processed PPG signal, wherein the processing of the PPG signal comprises:

identifying a frequency and phase associated with a pulsatile component of the PPG signal;

generating a matched signal based on the identified frequency and phase; and mixing the PPG signal with the matched signal; and analyzing, using the processor, the processed PPG signal to determine the respiration rate of the patient based on the amplitude modulation component.

2. The method of claim 1, wherein analyzing the processed PPG signal comprises:

transforming the processed PPG signal based at least in part on a continuous wavelet transform to generate a scalogram;

identifying for a particular time, a scale in the scalogram associated with respiration information; and determining the respiration rate based at least in part on the scale.

3. The method of claim 1, wherein analyzing the processed PPG signal comprises performing a Fourier transform to identify a frequency associated with the amplitude modulation component.

4. A non-transitory computer-readable storage medium for use in determining respiration rate for a patient, the computer-readable medium comprising:

computer program instructions recorded thereon for causing a processor to:

receive a photoplethysmograph (PPG) signal from a pulse oximetry sensor that is configured to photoelectrically sense absorption of light in tissue of the patient, wherein the PPG signal includes an amplitude modulation component caused at least in part by respiration;

process the PPG signal to move the amplitude modulation component into a baseline component of the PPG signal to generate a processed PPG signal, wherein the processing of the PPG signal comprises:

identifying a frequency and phase associated with a pulsatile component of the PPG signal;

generating a matched signal based on the identified frequency and phase; and mixing the PPG signal with the matched signal; and analyze the processed PPG signal to determine the respiration rate based on the amplitude modulation component.

5. The computer-readable medium of claim 4, wherein analyzing the processed PPG signal comprises:

transforming the processed PPG signal based at least in part on a continuous wavelet transform to generate a scalogram;

identifying for a particular time, a scale in the scalogram associated with respiration information; and determining the respiration rate based at least in part on the scale.

6. The computer-readable medium of claim 4, wherein analyzing the processed PPG signal comprises performing a Fourier transform to identify a frequency associated with the amplitude modulation component.

7. A patient monitoring system comprising a processor configured to:

receive a photoplethysmograph (PPG) signal from a pulse oximetry sensor that is configured to photoelectrically sense absorption of light in tissue of a patient, wherein the PPG signal includes an amplitude modulation component caused at least in part by respiration;

process the PPG signal to move the amplitude modulation component into a baseline component of the PPG signal to generate a processed PPG signal, wherein the processing of the PPG signal comprises:

identifying a frequency and phase associated with a pulsatile component of the PPG signal;

generating a matched signal based on the identified frequency and phase; and mixing the PPG signal with the matched signal to generate the processed PPG signal; and analyze the processed PPG signal to determine the respiration information rate of the patient based on the amplitude modulation component.

8. The patient monitoring system of claim 7, wherein the pulse oximeter is configured to:

transform the processed PPG signal based at least in part on a continuous wavelet transform to generate a scalogram;

identify for a particular time, a scale in the scalogram associated with respiration information; and determine the respiration rate based at least in part on the scale.

9. The patient monitoring system of claim 7, wherein the pulse oximeter is configured to perform a Fourier transform to identify a frequency associated with the amplitude modulation component.

* * * * *